US008603807B2

(12) United States Patent
Reed

(10) Patent No.: US 8,603,807 B2
(45) Date of Patent: Dec. 10, 2013

(54) METHODS OF MAKING MODULAR FUSION PROTEIN EXPRESSION PRODUCTS

(75) Inventor: Thomas D. Reed, Blacksburg, VA (US)

(73) Assignee: Intrexon Corporation, Blacksburg, VA (US)

( * ) Notice: Subject to any disclaimer, the term of this patent is extended or adjusted under 35 U.S.C. 154(b) by 200 days.

(21) Appl. No.: 12/090,463

(22) PCT Filed: Oct. 19, 2006

(86) PCT No.: PCT/US2006/060065
§ 371 (c)(1),
(2), (4) Date: Nov. 12, 2008

(87) PCT Pub. No.: WO2007/076166
PCT Pub. Date: Jul. 5, 2007

(65) Prior Publication Data

US 2009/0123973 A1 May 14, 2009

Related U.S. Application Data

(60) Provisional application No. 60/728,259, filed on Oct. 19, 2005.

(51) Int. Cl.

| | |
|---|---|
| ***C12N 15/00*** | (2006.01) |
| *C12P 1/00* | (2006.01) |
| *C12P 21/04* | (2006.01) |
| *C12P 21/06* | (2006.01) |
| *C07H 19/00* | (2006.01) |
| *C07H 21/00* | (2006.01) |
| *C07H 21/02* | (2006.01) |
| *C07H 21/04* | (2006.01) |

(52) U.S. Cl.
USPC ........ 435/320.1; 435/41; 435/69.1; 435/69.7; 536/23.1; 536/23.4; 536/22.1

(58) Field of Classification Search
None
See application file for complete search history.

(56) References Cited

U.S. PATENT DOCUMENTS

| | | | | |
|---|---|---|---|---|
| 4,661,454 | A | 4/1987 | Botstein et al. | |
| 4,820,642 | A | 4/1989 | Edman et al. | |
| 5,061,628 | A | 10/1991 | Roberts et al. | |
| 5,192,676 | A | 3/1993 | Morgan | |
| 5,736,135 | A | 4/1998 | Goeddel et al. | |
| 5,787,104 | A | 7/1998 | Kamiyama et al. | |
| 5,919,667 | A | 7/1999 | Gage et al. | |
| 6,096,523 | A | 8/2000 | Parrott et al. | |
| 6,184,000 | B1 * | 2/2001 | Jones et al. | 435/91.41 |
| 6,245,545 | B1 | 6/2001 | Kong et al. | |
| 6,248,569 | B1 | 6/2001 | Dunn et al. | |
| 6,514,737 | B1 | 2/2003 | Zhu et al. | |
| 6,562,624 | B2 | 5/2003 | Adachi et al. | |
| 7,785,871 | B2 | 8/2010 | Reed | |
| 2002/0146733 | A1 | 10/2002 | Sykes et al. | |
| 2003/0188345 | A1 | 10/2003 | Heim et al. | |
| 2004/0185556 | A1 | 9/2004 | Reed | |
| 2004/0253732 | A1 | 12/2004 | Lapize-Gauthey et al. | |
| 2005/0074883 | A1 * | 4/2005 | Slater et al. | 435/455 |
| 2005/0176099 | A1 | 8/2005 | Saha et al. | |
| 2005/0227316 | A1 | 10/2005 | Santi et al. | |
| 2008/0050808 | A1 | 2/2008 | Reed et al. | |
| 2008/0085553 | A1 | 4/2008 | Reed et al. | |
| 2008/0241915 | A1 | 10/2008 | Reed | |
| 2009/0170727 | A1 | 7/2009 | Reed | |
| 2009/0226976 | A1 | 9/2009 | Reed | |

FOREIGN PATENT DOCUMENTS

| | | | |
|---|---|---|---|
| GB | 2 393 441 | A | 3/2004 |
| WO | WO 01/07633 | A1 | 2/2001 |
| WO | WO 02/006834 | A2 | 1/2002 |
| WO | WO 2004/009761 | A2 | 1/2004 |
| WO | WO 2005/001025 | A2 | 1/2005 |
| WO | WO 2005/040336 | A2 | 5/2005 |
| WO | WO 2005/116231 | A1 | 12/2005 |
| WO | WO 2007/038276 | A2 | 4/2007 |
| WO | WO 2007/076166 | A3 | 7/2007 |

OTHER PUBLICATIONS

Appendix. NEB catalog 1995.*
Etheridge et al (JBC, 2002. vol. 277, No. 27, pp. 24764-24770).*
Schuller et al (Structural Biology, 1995. vol. 2, No. 1, pp. 69-76).*
Office Action mailed Oct. 23, 2009 in U.S. Appl. No. 10/682,764, inventor Reed, T., filed Oct. 9, 2003.
Notice of Allowance and Issue Fee Due mailed Mar. 2, 2010 in U.S. Appl. No. 10/682,764, inventor Reed, T., filed Oct. 9, 2003.
Office Action mailed Mar. 3, 2010 in U.S. Appl. No. 11/569,335, inventor Reed, T., filed Feb. 22, 2007.
Office Action mailed May 22, 2009 in U.S. Appl. No. 11/569,335, inventor Reed, T., filed Feb. 22, 2007.
Office Action mailed Feb. 19, 2010 in U.S. Appl. No. 11/841,380, inventor Reed, T., filed Aug. 20, 2007.
Office Action mailed Apr. 6, 2006 in U.S. Appl. No. 10/682,764, Reed et al., filed Oct. 9, 2003.
Office Action mailed Jul. 13, 2007 in U.S. Appl. No. 10/682,764, Reed et al., filed Oct. 9, 2003.

(Continued)

*Primary Examiner* — Jennifer Dunston
*Assistant Examiner* — Nancy J Leith
(74) *Attorney, Agent, or Firm* — Sterne, Kessler, Goldstein & Fox P.L.L.C.

(57) ABSTRACT

The invention relates to methods of making modular chimeric protein expression products and compositions utilized in the methods. In particular, the invention relates to sequential, directional cloning of polynucleotides encoding polypeptide modules. Each clonable element or module contains an open reading frame of interest flanked by predetermined restriction sites. The methods include using modules and vectors containing these modules as starting materials for recombinant DNA techniques. One advantage of the invention is that it allows for many variations of fusion proteins to be made quickly and easily without needing to design and evaluate each subsequent cloning step.

33 Claims, 15 Drawing Sheets

(56) References Cited

OTHER PUBLICATIONS

Office Action mailed Dec. 5, 2007 in U.S. Appl. No. 10/682,764, Reed et al., filed Oct. 9, 2003.
Office Action mailed Mar. 19, 2009 in U.S. Appl. No. 10/682,764, Reed et al., filed Oct. 9, 2003.
Office Action mailed Oct. 30, 2008 in U.S. Appl. No. 11/233,246, Reed, T., filed Sep. 22, 2005.
Office Action mailed May 22, 2009 in U.S. Appl. No. 11/569,335, Reed et al., filed Feb. 22, 2007.
U.S. Appl. No. 10/682,764, inventor Reed, T., filed Oct. 9, 2003, published as U.S. 2004/0185556 A1.
U.S. Appl. No. 11/233,246, inventor Reed, T., et al., filed Sep. 22, 2005, published as U.S. 2008-0050808 A1.
U.S. Appl. No. 11/840,297, inventor Reed, T., filed Aug. 17, 2007, published as U.S. 2008/0241915 A1.
U.S. Appl. No. 11/840,744, inventors Reed, T., et al., filed Aug. 17, 2007, published as U.S. 2008/0085553 A1.
U.S. Appl. No. 11/841,380, inventor Reed, T., filed Aug. 20, 2007.
U.S. Appl. No. 11/569,335, inventor Reed, T., filed May 18, 2005, published as US 2009/0170727 A1.
Asselburgs, F. and Rival, S., "Creation of a Novel, Versatile Multiple Cloning Site Cut by Four Rare-Cutting Homing Endonucleases, " *Biotechniques 20*:558-562, Informa Life Sciences Publishing (1996).
Bray, P.F., et al., "Physical linkage of the genes for platelet membrane glycoproteins *IIb and IIIa," Proc. Natl. Acad. Sci. 85*:8683-8687, National Academy of Sciences (1988).
Goderis, I., et al., "A set of modular plant transformation vectors allowing flexible insertion of up to six expression units," *Plant Molec. Biol. 50*:17-27, Kluwer Academic Publishers (2002).
Jayaraj et al., "GeMS: an advanced software package for designing synthetic genes," *Nucleic Acids Research 33*: 3011-3016, Oxford University Press, doi: 10.1093/nar/gki614 (May 23, 2005).
La Fontaine et al., "Eukaryotic Expression Vectors That Replicate to Low Copy Number in Bacteria: Transient Expression of the Menkes Protein," *Plasmid 39*: 245-251, Academic Press (1998).
Lin, L., et al., "Efficient linking and transfer of multiple genes by a multigene assembly and a transformation vector system," *Proc. Natl. Acad. Sci. 100*:5962-5967, National Academy of Science (2003).
Lu et al., "Vector NTI, a balanced all-in-one sequence analysis suite," *Briefings in Bioinformatics 5*: 378-388, Henry Stewart Publications (Dec. 2004).
Perera, S.C. et al., "An Analysis of Ecdysone Receptor Domains Required for Heterodimerization With Ultraspiracle," *Archives of Insect Biochemistry and Physiology 41*: 61-70, Wiley-Liss, Inc. (1999).
Thomson, M., et al., "Artificial Gene-Clusters Engineered into Plants Using a Vector Based on Intron- and Intein- encoded Endonucleases," *In Vitro Cell. Dev. Biol. 38*:537-542, Tissue Culture Association (Nov. 2002).
Zabarovska, V., "*Not*I passporting to identify a species composition of complex microbial systems," *Nucl. Acid Res. 31*:E5, Oxford University Press, DOI: 10.1093/narigng005, 10 pages (2003).
Office Action mailed Jul. 10, 2009 in U.S. Appl. No. 11/233,246, Reed, T., filed Sep. 22, 2005.
Two pages from the New England BioLabs Online Catalog, http://web.archive.org/web/20020408135531/www.neb.com/neb/frame_cat.html, printed on Jun. 22, 2009.
Office Action dated Sep. 1, 2010 in U.S. Appl. No. 11/841,380, inventor Thomas D. Reed, filed Aug. 20, 2007.
Office Action dated Sep. 30, 2010 in U.S. Appl. No. 11/569,335 inventor Thomas D. Reed, filed Feb. 22, 2007.
Office Action mailed Jul. 6, 2010 in U.S. Appl. No. 11/840,744, inventor Reed et al, filed Aug. 17, 2007.
Office Action dated Jul. 21, 2010 in U.S. Appl. No. 11/840,297, inventor Thomas D. Reed, filed Aug. 17, 2007.
Caras, I.W., et al., "Signal for Attachment of a Phospholipid Membrane Anchor in Decay Accelerating Factor," *Science 238*(4831):1280-1283, American Association for the Advancement of Science, United States (1987).
Helfrich, W., et al., "A rapid and versatile method for harnessing scFv antibody fragments with various biological effector functions," *J. Immunol. Methods 237*(12):131-145, Elsevier Science B.V., Netherlands (2000).
Parr, R.D. and Ball, J.M. "New donor vector for generation of histidine-tagged fusion proteins using the Gateway Cloning System," *Plasmid 49*(2):179-183, Elsevier Science (USA), United States (2003).
Dzivenu, O.K., et al., "General co-expression vectors for the overexpression of heterodimeric protein complexes in *Escherichia cole, "Protein Expression and Purification 38*: 1-8, Elsevier (2004).

* cited by examiner

| Site I | EXON R segment | Vestigial Sites | EXON T segment | Site II | stuffer | Site III |

| Site I | EXON D segment | Vestigial Sites | EXON A segment | Vestigial Sites | EXON H segment | Site II | stuffer | Site III |

| Site I | EXON A segment | Vestigial Sites | EXON P segment | Vestigial Sites | EXON L segment | Vestigial Sites | EXON C segment | Site II | stuffer | Site III |

| Site I | ORF Y | Vestigial Sites | ORF Z | Vestigial Sites | LOCALIZATION SIGNAL | Site II | stuffer | Site III |

| Site I | LOCALIZATION SIGNAL | Vestigial Sites | PEPTIDE 3 | Vestigial Sites | PEPTIDE 4 | Vestigial Sites | PEPTIDE 5 | Site II | stuffer | Site III |

| Site I | LIGAND X | Vestigial Sites | LIGAND X | Vestigial Sites | LIGAND X | Vestigial Sites | LOCALIZATION SIGNAL | Site II | stuffer | Site III |

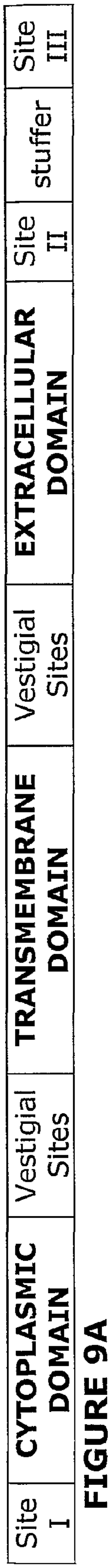

FIGURE 9A

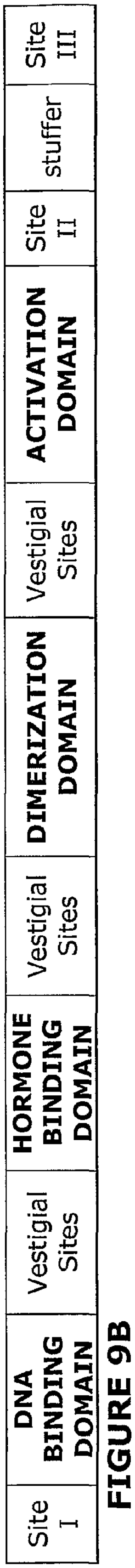

FIGURE 9B

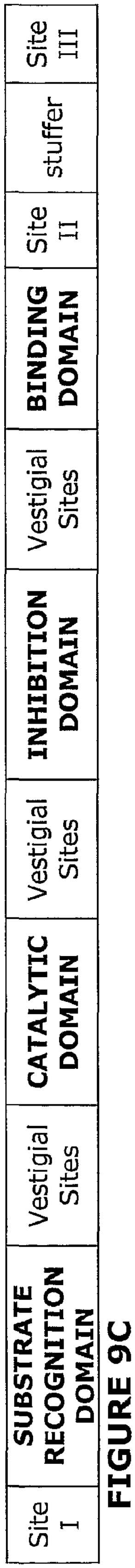

FIGURE 9C

| Site I | CYTOPLASMIC DOMAIN | Vestigial Sites | TRANSMEMBRANE DOMAIN | Vestigial Sites | EXTRACELLULAR DOMAIN | Site II | stuffer | Site III |

| Site I | DNA BINDING DOMAIN | Vestigial Sites | HORMONE BINDING DOMAIN | Vestigial Sites | DIMERIZATION DOMAIN | Vestigial Sites | ACTIVATION DOMAIN | Site II | stuffer | Site III |

| Site I | SUBSTRATE RECOGNITION DOMAIN | Vestigial Sites | CATALYTIC DOMAIN | Vestigial Sites | INHIBITION DOMAIN | Vestigial Sites | BINDING DOMAIN | Site II | stuffer | Site III |

FIGURE 10
PROMOTER
CHIMERIC PROTEIN CODING SEQUENCE
STOP
POLY-A

| <-------------- Module Open Reading Frame --------------> | | | | |
|---|---|---|---|---|
| NgoM IV | ORF of interest | Xma I | Stuffer | Cla I |
| GCCGGC | AAGAAGAAAAAGAAGAAG | CCCGGG | GGCGGAGGC | ATCGAT |
| AlaGly | LysLysLysLysLysLys | ProGly | GlyGlyGly | IleAsp |

FIGURE 11

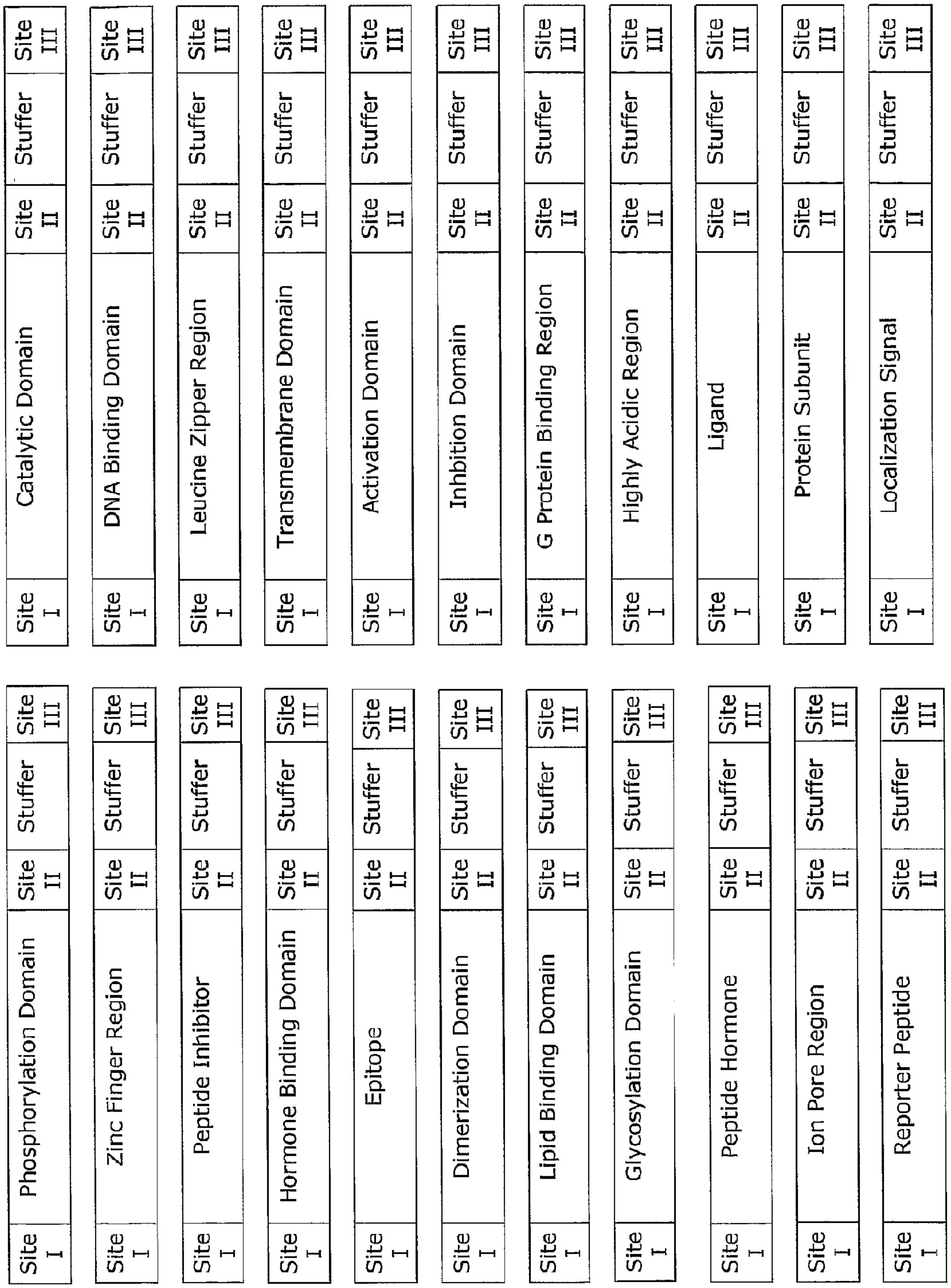

FIGURE 12

| Site I | Phosphorylation Domain | Site II | Stuffer | Site III |

| Site I | Zinc Finger Region | Site II | Stuffer | Site III |

| Site I | Peptide Inhibitor | Site II | Stuffer | Site III |

| Site I | Hormone Binding Domain | Site II | Stuffer | Site III |

| Site I | Epitope | Site II | Stuffer | Site III |

| Site I | Dimerization Domain | Site II | Stuffer | Site III |

| Site I | Lipid Binding Domain | Site II | Stuffer | Site III |

| Site I | Glycosylation Domain | Site II | Stuffer | Site III |

| Site I | Peptide Hormone | Site II | Stuffer | Site III |

| Site I | Ion Pore Region | Site II | Stuffer | Site III |

| Site I | Reporter Peptide | Site II |

METHODS OF MAKING MODULAR FUSION PROTEIN EXPRESSION PRODUCTS

This application is the U.S. national stage of International Application No. PCT/US2006/060065, filed Oct. 19, 2006, which claims the benefit of U.S. provisional Application No. 60/728,259, filed Oct. 19, 2005, which is incorporated by reference in its entirety.

REFERENCE TO SEQUENCE LISTING SUBMITTED ELECTRONICALLY VIA EFS-WEB

This application includes a "SequenceListing.ST25.txt", 2,111 bytes, created on Nov. 5, 2008, and submitted electronically via EFS-Web, which is hereby incorporated by reference in its entirety.

FIELD OF INVENTION

The invention relates to molecular biology methods and products for performing the methods. More specifically, the invention relates to methods of cloning nucleic acids that encode modular proteins, where modules may be added sequentially at predetermined locations.

This application has subject matter related to application Nos. 60/728,259, 60/803,913, 60/821,682, 60/821,958, Ser. No. 10/682,764 (US2004/0185556, PCT/US2004/013517, WO2005/040336), Ser. No. 11/233,246, and US20040572011P (WO2005116231). Each of these patents and applications is hereby incorporated by reference.

BACKGROUND AND PRIOR ART

Recombinant DNA technologies and molecular biological methods of cloning nucleic acids are known in the art. Such methods include manipulating nucleic acids using restriction endonucleases, ligases, nucleotide/nucleoside kinases and phosphatases, polymerases, and other molecular biology tools to generate desired recombinant nucleic acids. Several laboratory manuals have been written as reference books for molecular biology researchers. Examples of these reference manuals include, Sambrook, J., E. F. Fritsch and T. Maniatis, 1989. *Molecular Cloning: A Laboratory Manual,* 2nd. ed. Cold Spring Harbor, N.Y.: Cold Spring Harbor Laboratory Press; and Joseph Sambrook and David Russell, 2001. *Molecular Cloning: A Laboratory Manual,* 3rd ed. Cold Spring Harbor, N.Y.: Cold Spring Harbor Laboratory Press.

A problem in the art is the lack of methodology to engineer chimeric protein expression products where modular elements can be easily inserted at desired positions within a chimera. In general, while hybrid or chimeric proteins have been made successfully, the goal of synthesis has been towards final endpoint products, without building-in a predetermined mechanism to add more modules. An aspect of the invention addresses this problem by contemplating the future need for chimeras and variations thereof and making it possible to build them without starting from scratch for each one. One embodiment of the invention generally relates to methods of making fusion protein expression products. Another embodiment of the invention relates to methods of making fusion protein expression products with pre-engineered modules. Another aspect of the invention relates to building block molecules or modules, where modules are pre-designed to be capable of insertion into a chimeric protein expression cassette. The instant invention also contemplates libraries of engineered modules that can be utilized in the disclosed methods. In one embodiment, modules are made with predetermined restriction sites.

DETAILED DESCRIPTION OF POLYPEPTIDE AND POLYNUCLEOTIDE SEQUENCES

SEQ ID NO:1 is an example of a nucleic acid module. The module has the 5'-3' structure of: 5'-predetermined restriction site—open reading frame (ORF) of polypeptide of interest—predetermined restriction site—stuffer—predetermined restriction site-3'. The predetermined restriction sites and stuffer also encode amino acids in mammals and are in frame with the polypeptide of interest, therefore the entire module is a composite open reading frame. SEQ ID NO:1 is depicted in FIG. 11.

SEQ ID NO:2 is the polypeptide encoded by SEQ ID NO:1.

BRIEF DESCRIPTION OF DRAWINGS

FIGS. 9A-9C show examples of fusion proteins wherein modules contain different functional domains.

FIG. 11 shows an example module containing an open reading frame of interest (ORF) flanked by predetermined restriction sites and a stuffer.

FIG. 12 shows an example of a library of modules useful in the invention. The library members have identical predetermined restriction sites indicated as Site I, Site II and Site III. The open reading frames are not drawn to scale, and therefore may vary in length. In one embodiment, the library members are contained within vector DNA. In one embodiment the vector is a circular plasmid.

BRIEF DESCRIPTION OF THE INVENTION

Figure 1:
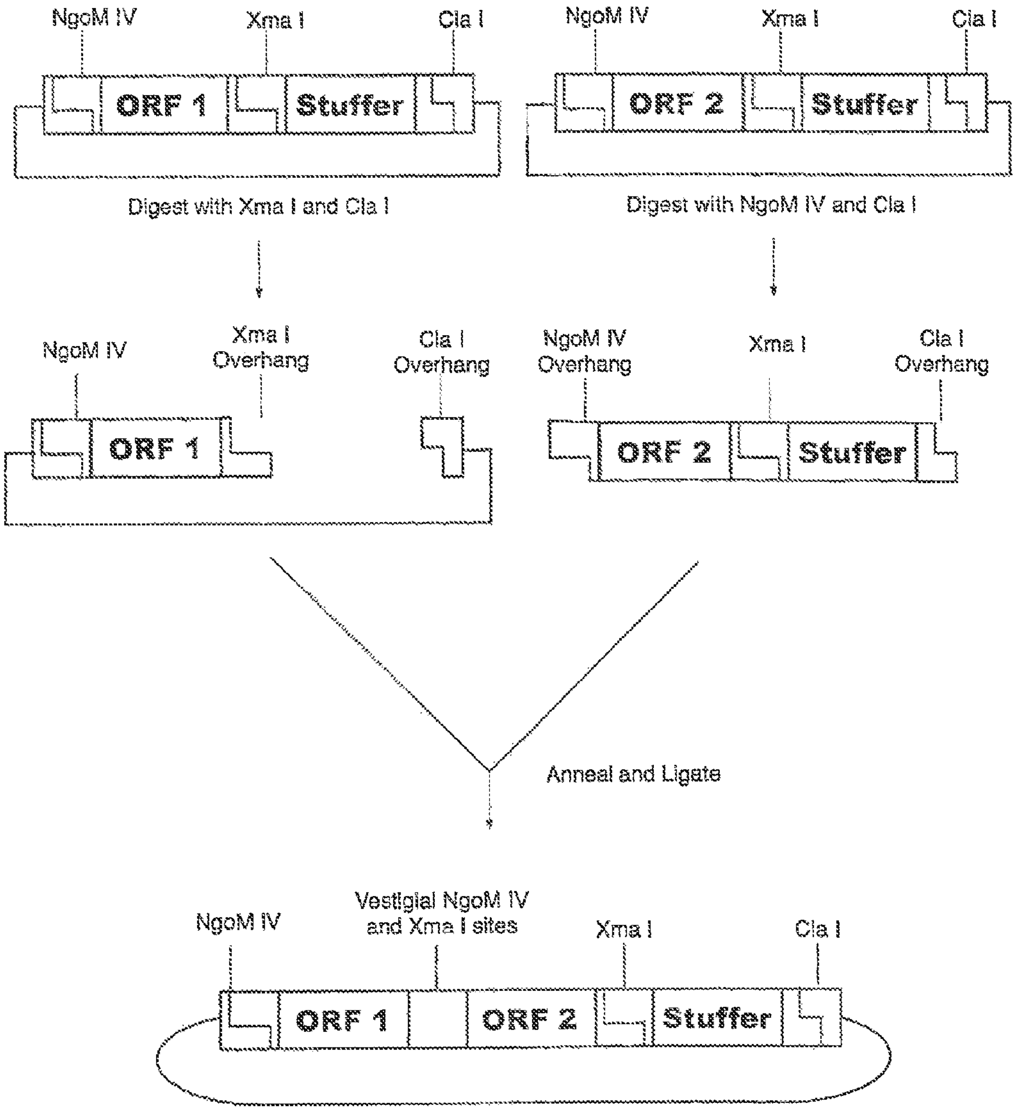
FIG. 1 shows a method for building fusion proteins in an N-terminus to C-terminus direction, utilizing two circular DNA starting reagents.

The invention relates to methods of making modular chimeric protein expression products and compositions utilized in the methods. In particular, the invention relates to sequential, directional cloning of polynucleotides encoding polypeptide modules. Each clonable element contains an open reading frame flanked by predetermined restriction sites. The methods include using clonable elements and vectors containing these elements as starting materials for recombinant DNA techniques. One advantage of the invention is that it allows for many variations of fusion proteins to be made quickly and easily without needing to design and evaluate each subsequent cloning step.

One embodiment of the invention generally relates to methods of making fusion protein expression products. Another embodiment of the invention relates to methods of making fusion protein expression products with combinatorial modules. Another aspect of the invention relates to building block molecules or modules, where modules are predesigned to be capable of insertion into a chimeric expression cassette. The instant invention also contemplates libraries of modules that can be utilized in the disclosed methods. In one embodiment, modules are made with predetermined restriction sites.

Each clonable element or module contains a polynucleotide sequence that encodes an open reading frame of interest, such as, but not limited to, a full length protein or polypeptide, or a functional domain, structural domain, enzymatic domain, inhibition domain, binding domain, localization signal, epitope, exon, or other desired subcomponent. A database directed to modular protein information available through the National Library of Medicine called Conserved Domain Database, or CDD, represents one resource for identifying domains based on amino acid sequence homology conserved across protein families and species.

Non-limiting examples of full length proteins include kinases, kinase subunits, phosphatases, phosphatase subunits, peptide ligands, proteases, protease subunits, enzyme subunits, DNA binding protein subunits, g-protein subunits, ion channel subunits, and membrane receptor subunits, to name a few.

Non-limiting examples of functional domains include DNA binding domains, transcription activation domains, dimerization domains, catalytic domains, phosphorylation domains, regulatory domains, death domains, pleckstrin homology domains, lipid binding domains, hormone binding domains, ligand binding domains, zinc finger regions, leucine zipper regions, g-protein binding domains, glycosylation domains, acylation domains, and transmembrane domains, to name a few.

Non-limiting examples of structural domains include alpha helical regions, beta sheet regions, acidic regions, basic regions, hydrophobic domains, intra-chain disulfide bonding domains, co-factor binding domain, and metal ion binding domain, to name a few.

Non-limiting examples of enzymatic domains include enzyme active sites, phosphorylation catalytic domains, phosphatase catalytic domains, adenylate cyclase catalytic domain, metabolic enzyme active sites, protease active sites, polymerase active sites, lipase active sites, glycolytic pathway enzyme active sites, nucleotide synthesis enzyme active sites, and amino acid synthesis enzyme active sites, to name a few.

Non-limiting examples of inhibition domains include kinase inhibitory subunit binding regions, phosphatase inhibitory subunit binding regions, and allosteric ligand binding regions to name a few.

Non-limiting examples of binding domains include steroid hormone binding domains, peptide hormone binding domains, substrate binding domains, ATP binding domains, PDZ domains, SH3 domains, SH2 domains, PB1 domains, drug binding domains, g-protein binding domains, DNA binding domains, lipid binding domains, carbohydrate binding domains, and dimerization domains to name a few.

Non-limiting examples of localization signals include endoplasmic reticulum localization signals, nuclear localization signals, mitochondrial localization signals, plasma membrane localization signals, and sarcoplasmic reticulum localization signals, to name a few.

Non-limiting examples of epitopes include hemagluttinin epitope, c-Myc epitope, $FLAG^R$, His6, acidic regions, basic regions, and antibody binding regions, to name a few.

In nature, protein domains often correlate with exons. It is thought that natural exon shuffling is one explanation for the presence of modular proteins in eukaryotes. An open reading frame of an exon, therefore, represents an open reading frame of interest according to the invention. One skilled in the art recognizes that some exons have split codons at the ends corresponding to splice sites. When this occurs, the portion or segment of the exon containing the correct open reading frame is the ORF of interest.

Modules may also contain polynucleotide sequences that encode peptides not found in nature, but nonetheless have a desired feature or property. As used herein, the term module means a nucleic acid that encodes an open reading frame comprising an open reading frame of interest flanked by predetermined restriction sites. When the methods and products of the invention are utilized in mammalian systems, the modules should lack mammalian stop codons.

The modules of the invention may be part of a larger polynucleotide such as a vector. Such vectors include but are not limited to circular plasmids, expression vectors, viral vectors, or artificial chromosomes. The predetermined restriction endonuclease sites in the modules are unique within the module. In one embodiment of the invention, the predetermined restriction sites of a module are unique within a vector or other nucleic acid comprising the module. In this context, the predetermined restriction sites provide unique cloning sites within a vector and provide directionality of module cloning.

DETAILED DESCRIPTION OF THE INVENTION

Many proteins are modular in nature. For instance, a nuclear receptor has domains including a DNA binding domain, a ligand binding domain, a dimerization domain and an activation domain. It is often desirable to make chimeric receptors by exchanging functional domains between the receptors so that domain functionality can be studied and/or new research and therapeutic tools can be made. It is also desirable to synthesize fusion proteins that have novel cellular or therapeutic activity. For example, chimeric polyligands that modulate protein kinase D activity have been designed and synthesized from a variety of heterologous protein sources (see 60/728,259).

An aspect of the invention relates to the combinatorial modularity of fusion proteins and preparing building blocks of open reading frames that may be incorporated into a fusion protein expression cassette at any desired location. In other words, the invention encompasses an inventory of components designed to be utilized together, in a manner analogous to LEGO® building blocks or interlocking modular flooring. Additional aspects of the invention are methods of making these modular fusion proteins easily and conveniently. In this regard, an embodiment of the invention includes methods of modular cloning of component protein domains.

For convenience of cloning, it is desirable to make modular elements that are compatible at cohesive ends and can be inserted and cloned sequentially. One embodiment of the invention accomplishes this by exploiting the natural properties of restriction endonuclease site recognition and cleavage. Another aspect of the invention encompasses modules with open reading frame flanking sequences that, on one side of the ORF, are utilized for restriction enzyme digestion once, and on the other side, utilized for restriction enzyme digestion as many times as desired. In other words, a predetermined restriction site in the module is utilized and destroyed in order to effect recursive, sequential cloning of modular elements.

EXAMPLE 1

Method Starting with Two Vectors

A modular fusion protein is made using the following method and starting with 2 reagents each containing an open reading frame (ORF) of interest flanked by predetermined restriction sites. An example of restriction sites flanking an ORF of interest are sequences recognized by the restriction enzymes NgoM IV and Cla I; or Xma I and Cla I (see FIG. 1). Referring to FIG. 1, one embodiment of the method utilizes two nucleic acid starting reagents. One reagent is circular DNA containing an open reading frame of interest (ORF 1) flanked on the 5' end by an NgoM IV site, and flanked on the 3' end, in order, by an Xma I site and a Cla I site. In other words, a first reagent comprises DNA with the following characteristics from 5' to 3':—NgoM IV-ORF 1-Xma I-stuffer-Cla I—. Further referring to FIG. 1, a second reagent is circular DNA also containing an open reading frame of interest (ORF 2) flanked on the 5' end by an NgoM IV site, and flanked on the 3' end, in order, by an Xma I site and a Cla I site. The stuffer represents nucleotides that allow enough space for two different restriction enzymes to bind and cleave the DNA. The term "stuffer" is synonymous with "spacer" and the two terms are used interchangeably herein. In general, the stuffer or spacer should be in frame with adjacent open reading frames, and therefore should have a length which is a multiple of three, since codons are three bases long. An example stuffer would be GGAGGCGGA (SEQ ID NO: 3), encoding GlyGlyGly. The stuffer/spacer may have other amino acid compositions.

An embodiment of a modular cloning method according to the invention includes cutting the first circular DNA reagent with Xma I and Cla I to yield linear DNA with a 3' Xma I overhang and a 5' Cla I overhang. This DNA fragment is the acceptor DNA and will accept an excised insert from the second circular DNA reagent. In a separate container, the second circular DNA reagent, called the donor, is cut with NgoM IV and Cla I to yield a released linear DNA with a 3' Cla I overhang and a 5' NgoM IV overhang. The second DNA fragment is then purified away from its linearized vector backbone DNA. These restriction digestions generate first and second DNA fragments with compatible cohesive ends.

Figure 2:
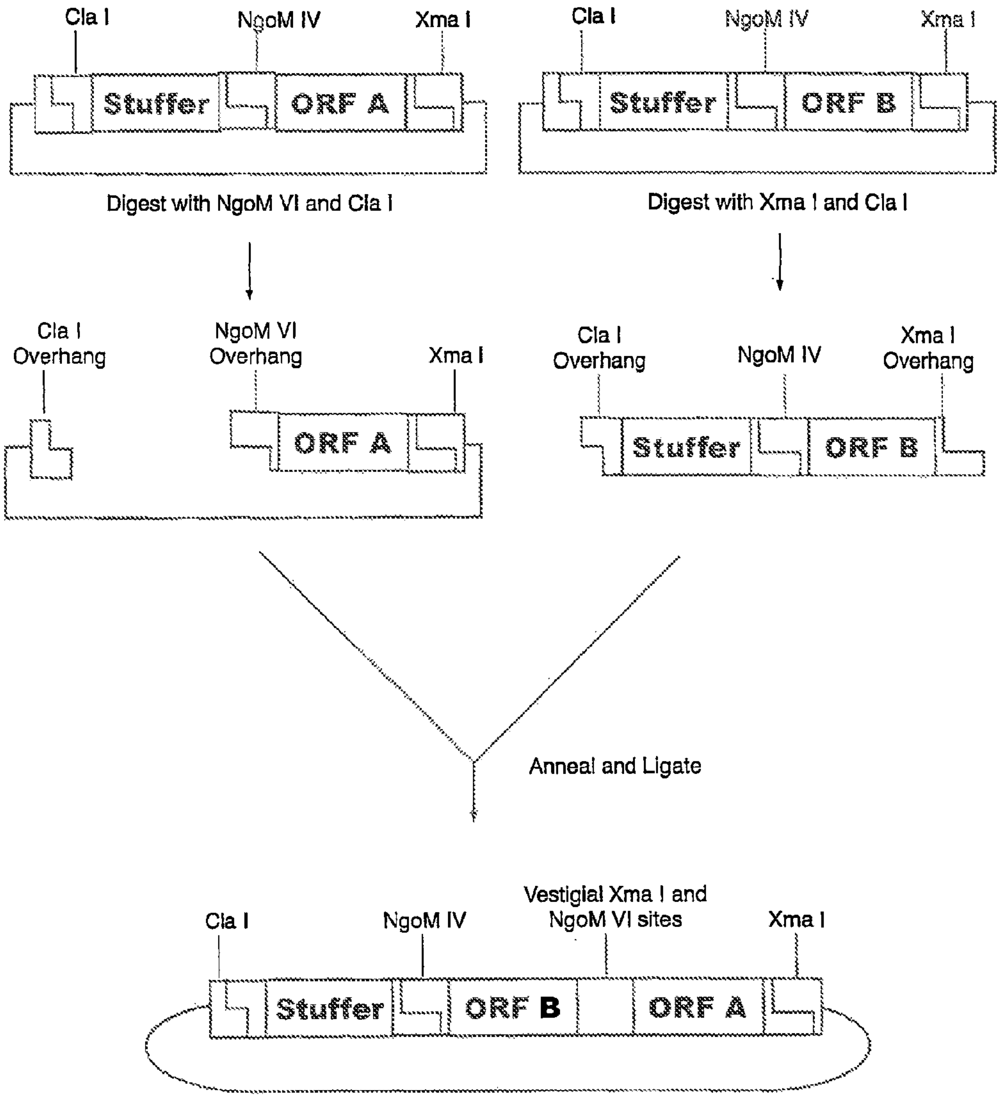
FIG. 2 shows a method for building fusion proteins in a C-terminus to N-terminus direction, utilizing two circular DNA starting reagents.

When these first and second DNA fragments are mixed together, annealed, and ligated to form a third circular DNA fragment, the Xma I site that was in the first DNA and the NgoM IV site that was in the second DNA are destroyed in the third circular DNA. Now this vestigial region of DNA is protected from further Xma I or NgoM IV digestion, but sequences flanking the resulting fused open reading frames in the third circular DNA still contain intact 5' NgoM IV, and 3' Xma I and Cla I sites which are useful in subsequent, recursive cloning steps. This process can be repeated numerous times to achieve directional, sequential, modular cloning events. In the example depicted in FIG. 1, the direction of module addition proceeds from N-terminus to C-terminus of the fusion protein; while in the example depicted in FIG. 2, the direction of module addition proceeds from C-terminus to N-terminus of the chimeric protein. Restriction sites recognized by NgoM IV, Xma I, and Cla I endonucleases represent a trio of sites that permit recursive, sequential cloning when used in a module.

Figure 4:
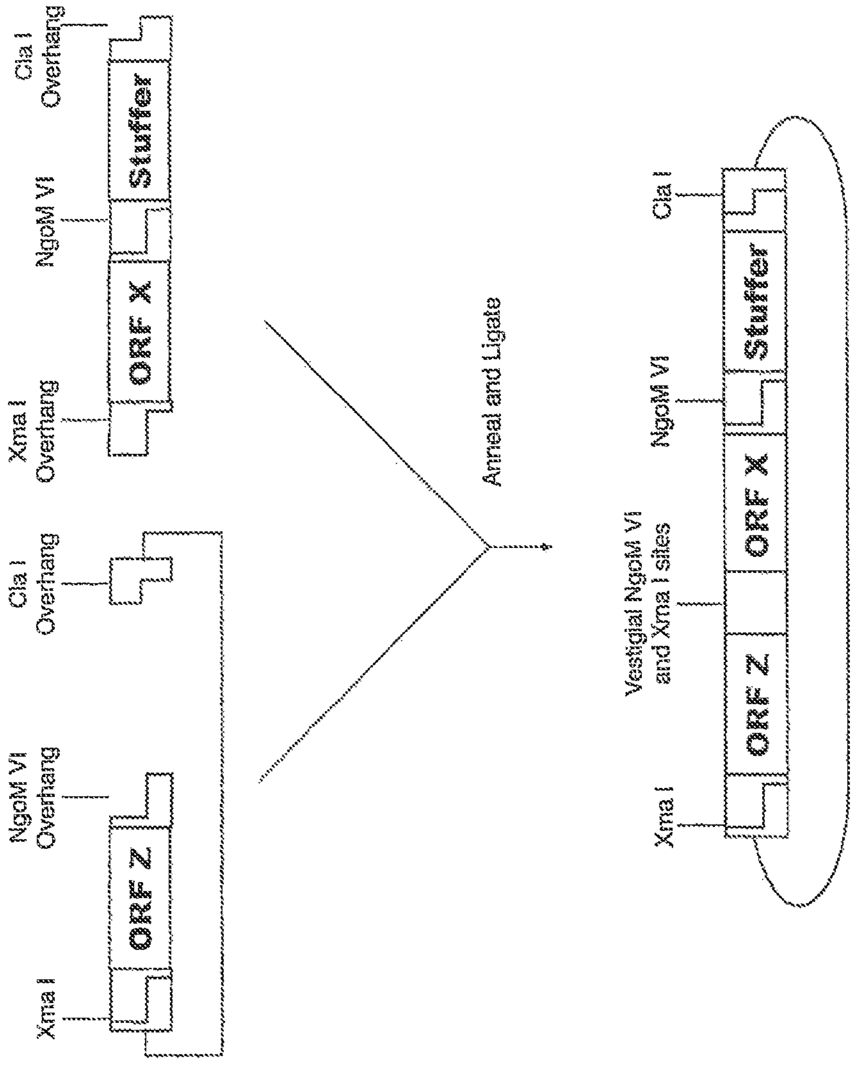
FIG. 4 shows a method for building fusion proteins in an N-terminus to C-terminus direction, utilizing two linear DNA starting reagents.

One skilled in the art recognizes that the NgoM IV site and the Xma I site can be swapped with each other as long as the order is consistent throughout the reagents (see FIG. 4 for example). One of ordinary skill in the art also recognizes that other restriction site groups can accomplish sequential, directional cloning as described herein. Preferred criteria for selecting restriction endonucleases are 1) selecting a pair of endonucleases that generate compatible cohesive ends but whose sites are destroyed upon ligation with each other; 2) selecting a third restriction endouclease that does not generate sticky ends compatible with either of the first two. When such criteria are utilized as a system for sequential, directional cloning, protein subdomains, modules, and other coding regions or expression components can be combinatorially assembled as desired.

With respect to selection criterium number 1 above, other restriction endonucleases may be employed to accomplish this method. For example, NgoM IV, Xma I, TspM I, BspE I, and Age I all create complementary overhangs when they cut DNA containing their respective recognition sites. Therefore, in general, any two of these enzymes whose recognition sites are destroyed when annealed and ligated can be utilized as a pair in the same way as NgoM IV and Xma I are used in this example and other examples described herein.

Additional criteria to restriction endonuclease selection may include codon usage/bias with respect to the species in which the fusion protein will be expressed. In one embodiment NgoM IV and Xma I are a preferred pair because they both utilize codons recognized by mammalian cells. Additional selection criteria may also include the properties of the amino acids encoded by the codons. For instance, it may be desirable to avoid restriction endonuclease sites whose codons encode charged amino acids. In the embodiment shown in FIG. 1, NgoM IV and Xma I are a preferred pair because the amino acids encoded are relatively bioneutral: NgoM IV encodes AlaGly in mammals and Xma I encodes ProGly in mammals (see also FIG. 11). One skilled in the art will recognize that the method is adaptable for other species by utilizing codons used in other species.

EXAMPLE 2

Method Starting With One Vector

Figure 3:
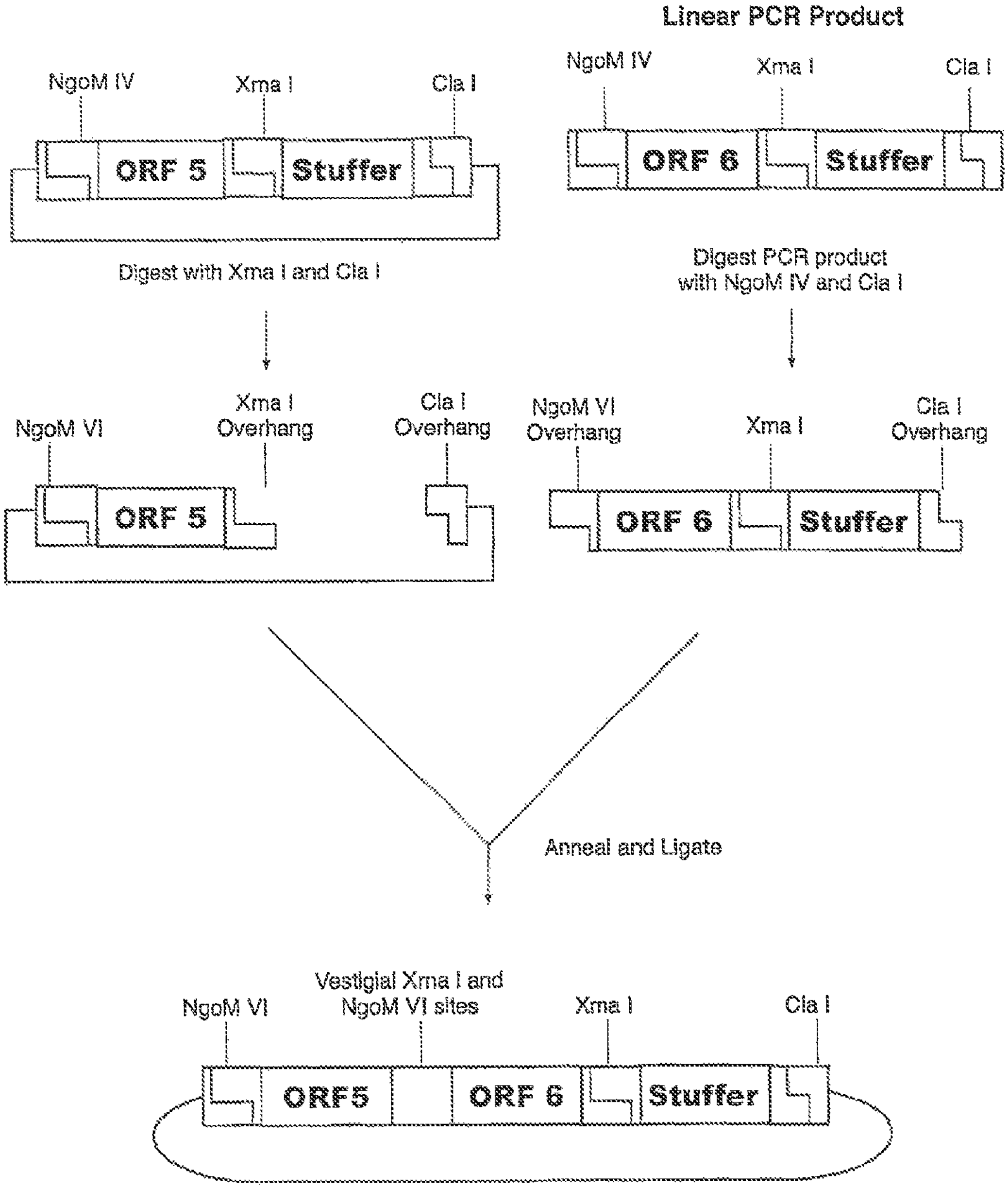
FIG. 3 shows a method for building fusion proteins in an N-terminus to C-terminus direction, utilizing one circular DNA starting reagent and one linear DNA starting reagent.

Another way to assemble coding region modules directionally and sequentially employs linear DNA in addition to circular DNA. For example, like the sequential cloning process described above, restriction sites flanking a coding region are sequences recognized by the restriction enzymes NgoM IV and Cla I; or Xma I and Cla I. Referring to FIG. 3, a first circular DNA reagent is cut with Xma I and Cla I to yield linear DNA with a 3' Xma I overhang and a 5' Cla I overhang. The first DNA reagent is the acceptor. A second reagent is a linear double-stranded DNA fragment generated by synthesizing and annealing complimentary oligonucleotides or by PCR amplification followed by digestion with appropriate restriction enzymes to generate overhangs. The second linear DNA has 3' Cla I overhang and a 5' NgoM IV overhang, which are compatible with cohesive ends of the first linearized DNA acceptor.

When these first and second DNA fragments are mixed together, annealed, and ligated to form a third circular DNA, the Xma I site that was in the first DNA and the NgoM IV site that was in the second DNA are destroyed in the third circular DNA. However, sequences flanking the resulting fusion protein of interest (ORF 5-ORF 6) in the third circular DNA still contain intact 5' NgoM IV, and 3' Xma I and Cla I sites which may be utilized subsequently in successive cloning steps. This process can be repeated numerous times to achieve directional, sequential, modular cloning events (see FIG. 5). Restriction sites recognized by NgoM IV, Xma I, and Cla I endonucleases represent a trio of sites that permit recursive modular cloning when used as flanking sequences.

EXAMPLE 3

Method Starting With Two Linear Double-stranded DNAs

The method of the invention can also be performed with two linear DNAs as starting reagents. In this example, the NgoM IV and Xma I sites have been swapped as compared to other examples herein. Referring to FIG. 4, the two starting reagents are 1) a vector backbone with a 3' NgoM IV overhang and a 5' Cla I overhang, wherein an open reading frame of interest, ORF Z, is positioned upstream of the NgoM IV site and an Xma I site is positioned in frame and upstream of ORF Z, and 2) double-stranded DNA open reading frame containing a 5' Xma I overhang and a 3' Cla I overhang, wherein the Xma I overhang is immediately upstream and in frame with open reading frame of interest, ORF X, and wherein ORF X is followed downstream by an NgoM IV site also in frame with ORF X. The two starting reagents may be provided or synthesized various ways. For example, by restriction endonuclease digestion, chemical synthesis, PCR amplification, to name a few. The overhangs present in the reagents may be a product of restriction endonuclease digestion or may be added to the ends as a linker or adapter as is known in the art. The result of annealing and ligating the two starting reagents is a chimeric polypeptide (ORF Z-ORF X) flanked upstream by an intact Xma I site and downstream by intact NgoM IV and Cla I sites, allowing the process to be repeated if it becomes desirable to add one or more modules. The ligated NgoM IV/Xma I region (indicated as vestigial NgoM IV, Xma I site) can no longer be cut by NgoM IV nor Xma I and is therefore protected from further digestion by these enzymes.

EXAMPLE 4

Module Libraries

The starting reagents discussed in the above examples may be members of a collection or library of reagents. Members of the collection share a number of characteristics. The minimal characteristics shared include identical predetermined restriction sites (NgoM IV, Xma I, Cla I, for example) flanking the open reading frames of interest. Also, the open reading frames of interest are engineered to lack these same restriction sites internally. Furthermore, at least the first starting reagent (acceptor DNA) is a circular DNA and is engineered to contain these same restriction sites only once in the entire circular DNA, namely at the open reading frame of interest flanking sites. In other words, the acceptor DNA vector is engineered to lack these predetermined restriction sites elsewhere.

In one embodiment of the invention, both the donor and acceptor reagents are circular DNA and are identical except for the open reading frame of interest. In another embodiment, the donor circular DNA reagent is not identical to the acceptor DNA reagent, in that the ORF of interest flanking restriction sites, while are absent from the ORF of interest, are not unique within the circular DNA molecule. This is possible because the released insert will be purified away from the rest of the vector.

One of ordinary skill in the art recognizes that the NgoM IV site and the Xma I site can be swapped with each other as long as the order is consistent throughout the reagents. One of ordinary skill in the art also recognizes that other restriction site groups may be utilized.

In one embodiment, the library members have modules containing open reading frames of interest composed of mammalian codons surrounded by predetermined restriction sites encoding amino acids in frame with the open reading frame and whose codons are utilized by mammals. FIG. 11 illustrates an embodiment of such a library member having a polylysine ORF of interest. As one can see from FIG. 11, the NgoM IV recognition sequence (GCCGGC, SEQ ID NO: 4) encodes AlaGly; the ORF (AAGAAGAAAAAGAAGAAG. SEQ ID NO: 5) encodes LysLysLysLysLysLys (SEQ ID NO: 6); the Xma I recognition sequence (CCCGGG, SEQ ID NO: 7) encodes ProGly; the stuffer (GGCGGAGGC, SEQ ID NO: 8) encodes GlyGlyGly; the Cla I recognition sequence (ATCGAT, SEQ ID NO: 9) encodes IleAsp. Therefore, the module itself is an open reading frame which contains an ORF of interest. The library of modules is engineered to be consistent with respect to the restriction sites flanking each open reading frame of interest so that modules may be inserted without having to design each successive cloning step. The variable components of the library include the open reading frame of interest and the stuffer/spacer component of a module, with the provision that all components should utilize codons from the species intended to express the fusion protein, and that every ORF of interest lacks the predetermined restriction sites.

The library of modules of the instant invention is distinct from other libraries known in the art, such as cDNA libraries. While cDNA libraries generally contain protein coding sequences flanked by vector restriction sites, the protein coding sequences are not necessarily open reading frames; the vector restriction sites flanking the protein coding sequences have not been engineered to be absent from the protein coding sequence, nor are these restriction sites engineered to be in frame with the adjacent coding sequence, nor do the restriction sites permit recursive cloning steps according to the invention. The library of the invention is further distinct from cDNA libraries in that cDNA libraries have non-coding sequences such as 3' and 5' untranslated regions (UTRs). FIG. 12 shows an example of a library of modules useful in the invention.

EXAMPLE 5

Building a Homomultimeric Fusion Protein

Figure 5:
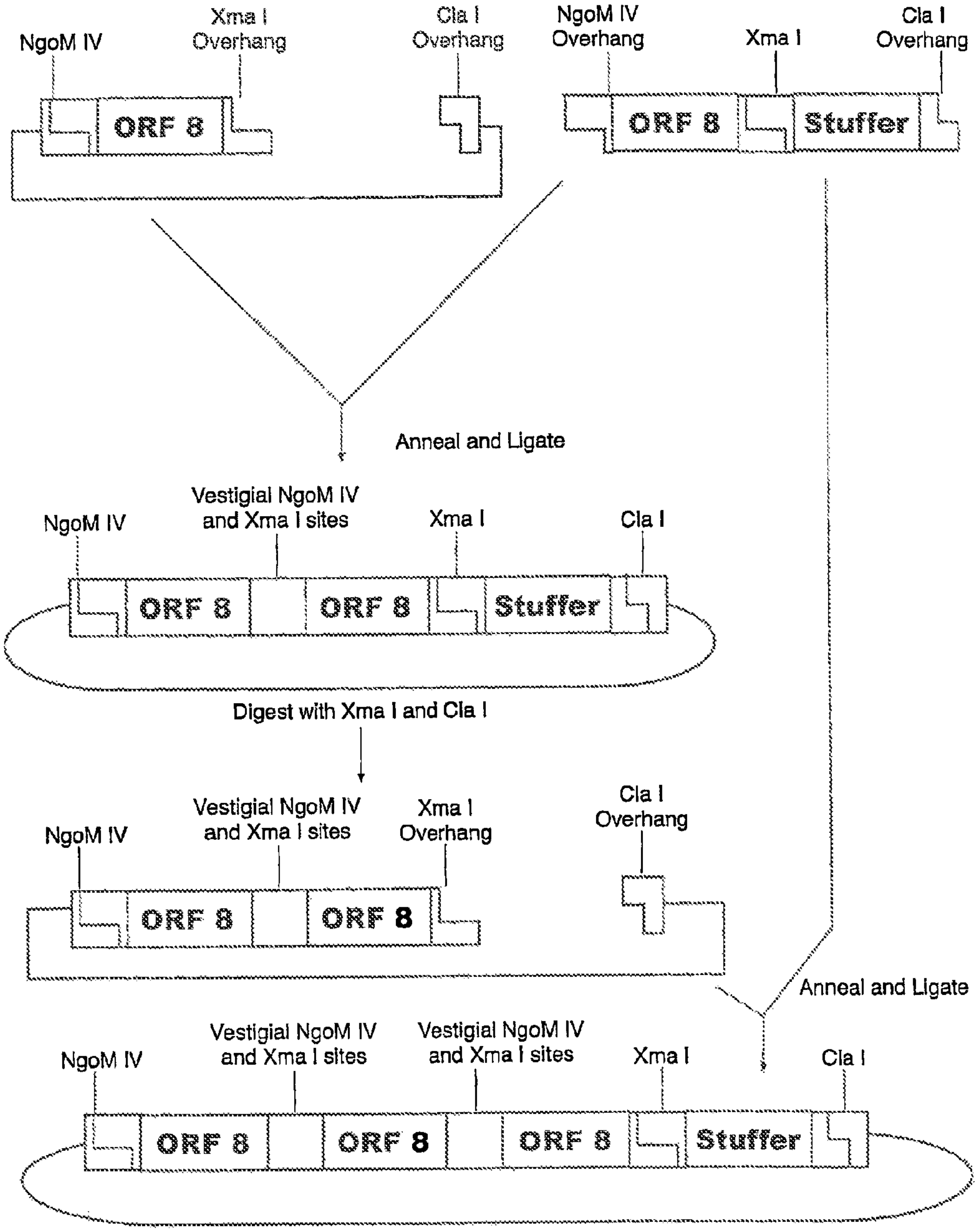
FIG. 5 shows a recursive method for building fusion proteins in an N-terminus to C-terminus direction.

An example of a homomultimeric fusion protein is a polypeptide comprising a dimer or multimer of, for example, ORF 8 (see FIG. 5). The open reading frame of interest, ORF 8, can be of any length or composition. For example, ORF 8 can be a peptide inhibitor of protein kinase D. When building a homomultimer from a circular DNA according to the invention, the two nucleic acid starting reagents are identical. However, two separate restriction digestions are performed. Utilizing the same exemplary restriction site positions in Example 1, one digestion with Xma I and Cla I is carried out in one container and another digestion with NgoM IV and Cla I is carried out in another container. Mixing the linearized vector DNA with the released insert, annealing, and ligating results in a fusion dimer of ORF 8. These steps can be repeated a number of times until the desired number of modules is achieved. Also, as illustrated in FIG. 5, one may start with two linear DNA molecules. One skilled in the art will recognize the variations available to the method.

EXAMPLE 6

Building a Heteromultimeric Fusion Protein

Figure 6A:
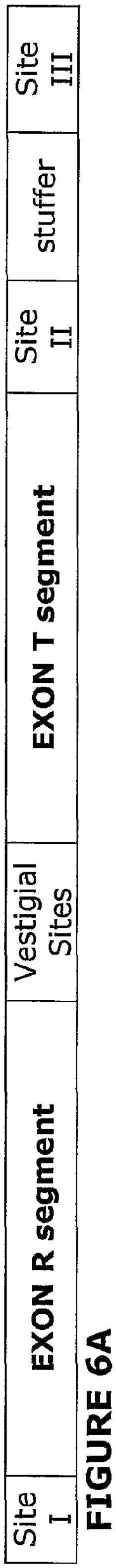
FIGS. 6A-6C show examples of chimeric polypeptides wherein modules are derived from portions of exons.
Figure 6B:
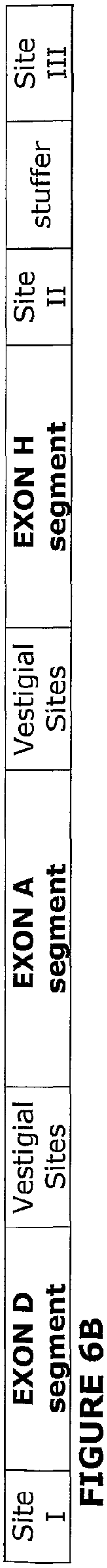
Figure 6C:
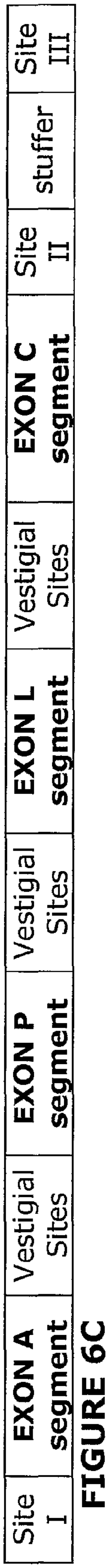
Figure 7A:
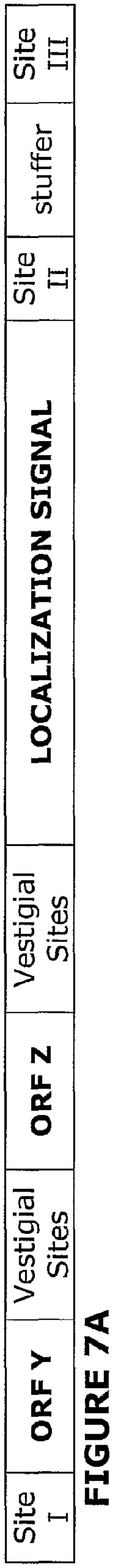
FIGS. 7A-7C show examples of chimeric polypeptides wherein one module contains a localization signal.
Figure 7B:
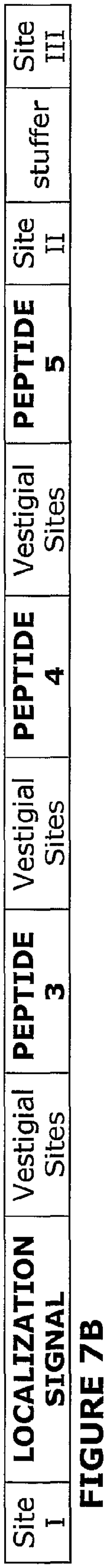
Figure 7C:
Figure 8A:
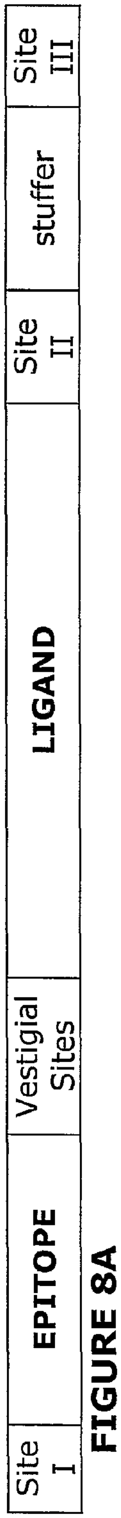
FIGS. 8A-8C show examples of fusion proteins wherein one module contains an epitope tag.
Figure 8B:
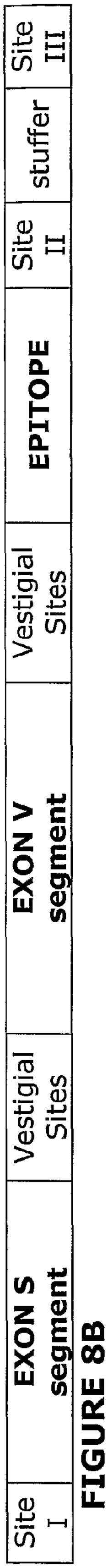
Figure 8C:
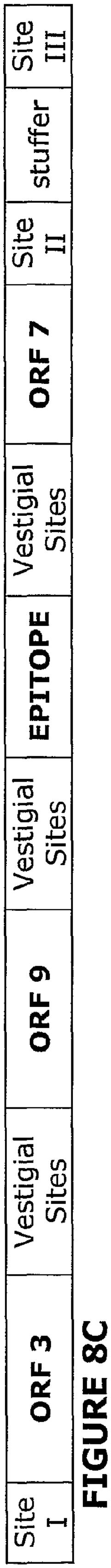
Figure 10:
FIG. 10 shows an example expression cassette containing a chimeric protein coding sequence made according to the methods of the invention.

An example of a heteromultimeric fusion protein is a polypeptide comprising at least two non-identical modules. FIGS. 6A-6C illustrate some heteromultimeric fusion proteins built from modules containing exon-derived ORFs of interest. FIGS. 7A-7C show examples of fusion polypeptides where one module contains a localization signal. FIGS. 8A-8C show examples of chimeric polypeptides wherein one module contains an epitope tag. FIGS. 9A-9C show examples of chimeric proteins built from modules containing different functional domains. Any of the methods described herein may be used to prepare heteromultimeric fusion proteins. Furthermore, the fusion proteins may then be expressed in mammalian cells. FIG. 10 shows an example expression cassette containing a chimeric protein coding sequence made according to the invention. The fusion proteins are useful as research tools or as therapeutics.

EXAMPLE 7

Stepwise Combinatorial Synthesis

The methods of the invention are useful for the combinatorial synthesis of several heteromultimers simultaneously. While the digestion, purification, mixing and ligating steps are as described above, the reaction containers are combined as follows. This example is a synthesis of every possible heteromultimer fusion protein assembled from four circular DNA starting reagents, each containing a different module coding sequence designated as moduleA, moduleB, moduleC, and moduleD. For instance, the resultant heteromultimers will ideally number $4^4$, and include moduleA-moduleB-moduleC-moduleD; moduleB-moduleC-moduleD-moduleA; moduleC-moduleA-moduleD-moduleB; etc. as well as homomultimers of each module.

The four different circular DNA acceptor reagents are linearized by cutting with Xma I and Cla I, each in a separate container. In another four separate containers, four different insert donors are cut with NgoM IV and Cla I. The inserts released from the donor digestions are purified to obtain four DNAs encoding moduleA, moduleB, moduleC, and moduleD with NgoM IV and Cla I overhangs. The next step is to mix an aliquot of each of the inserts with each acceptor in the same acceptor container. Each acceptor is therefore getting four different aliquots. The molarity of each insert added to the each acceptor is an amount effective to achieve desired stoichiometries. For example, if one wanted to make roughly the same number of each type of heteromultimer, one would add roughly the same number of moles of each of the four donor inserts. Insert size, composition, and other factors may affect the number of moles added. After annealing and ligating these four mixtures, the following dimer fusions are produced.

From the acceptor containing moduleA:
moduleA-moduleA
moduleA-moduleB
moduleA-moduleC
moduleA-moduleD From the acceptor containing moduleB:
moduleB-moduleA
moduleB-moduleB
moduleB-moduleC
moduleB-moduleD From the acceptor containing moduleC:
moduleC-moduleA
moduleC-moduleB
moduleC-moduleC
moduleC-moduleD From the acceptor containing moduleD:
moduleD-moduleA
moduleD-moduleB
moduleD-moduleC
moduleD-moduleD Since the junction connecting the modules of the fusion protein DNA cannot be digested with the predetermined restriction enzymes used in this example, more inserts can be added by repeating the above steps of linearization and aliquot addition. The method of combinatorial synthesis is useful for generating large numbers of chimeras simultaneously. The chimeras can then be tested in cells.

EXAMPLE 8

Dynamic Combinatorial Synthesis

In addition to the methods above, the module libraries of the invention may be utilized in dynamic combinatorial synthesis which will also generate large numbers of chimeras simultaneously. Dynamic combinatorial synthesis takes place when many compatible overhangs are present in the same reaction mixture and are allowed to anneal and ligate to each other. In contrast to the recursive methods described above, where a fusion protein is built N-terminus to C-terminus (or vice versa), the dynamic method results in inserts being joined in backwards and forwards orientations and in no particular order. While the two ends of the fusion protein constructs are anchored by chosen modules (analogous to first and second reagents as use above), the "middle" part of the fusion proteins are variable.

In the simplest example of dynamic combinatorial synthesis, an acceptor DNA reagent from the library of reagents according to the invention is digested with Xma I and Cla I. A second DNA reagent is then digested with NgoM IV and Cla I. Additionally, a third DNA reagent, also from the library, is digested with Xma I and NgoM IV. The second and third digested DNAs are isolated such that the polynucleotide containing the ORF of interest is kept. The next step is to mix together, anneal and ligate the first, second and third DNA reagents. Because the third reagent can anneal in two different directions with the first and second reagents because of its NgoM IV and Xma I overhangs, the resulting fusion proteins will have a "middle" with two different orientations.

A more complex example of dynamic combinatorial synthesis involves mixing together multiple modules that have been cut with NgoM IV and Xma I with first and second reagents digested as discussed above. When multiple DNAs with these overhangs are annealed and ligated, bidirectional orientations occur with each module. For instance, if five modules predigested with NgoM IV and Xma I are mixed together in roughly stoichiometric amounts, annealed, and ligated, each of the five modules should be present in all possible orders and orientations. Furthermore, the overall length of the "middle" section of the fusion protein will vary as well, since one or more modules may be absent from or present multiple times in a fusion protein.

Figure 13:
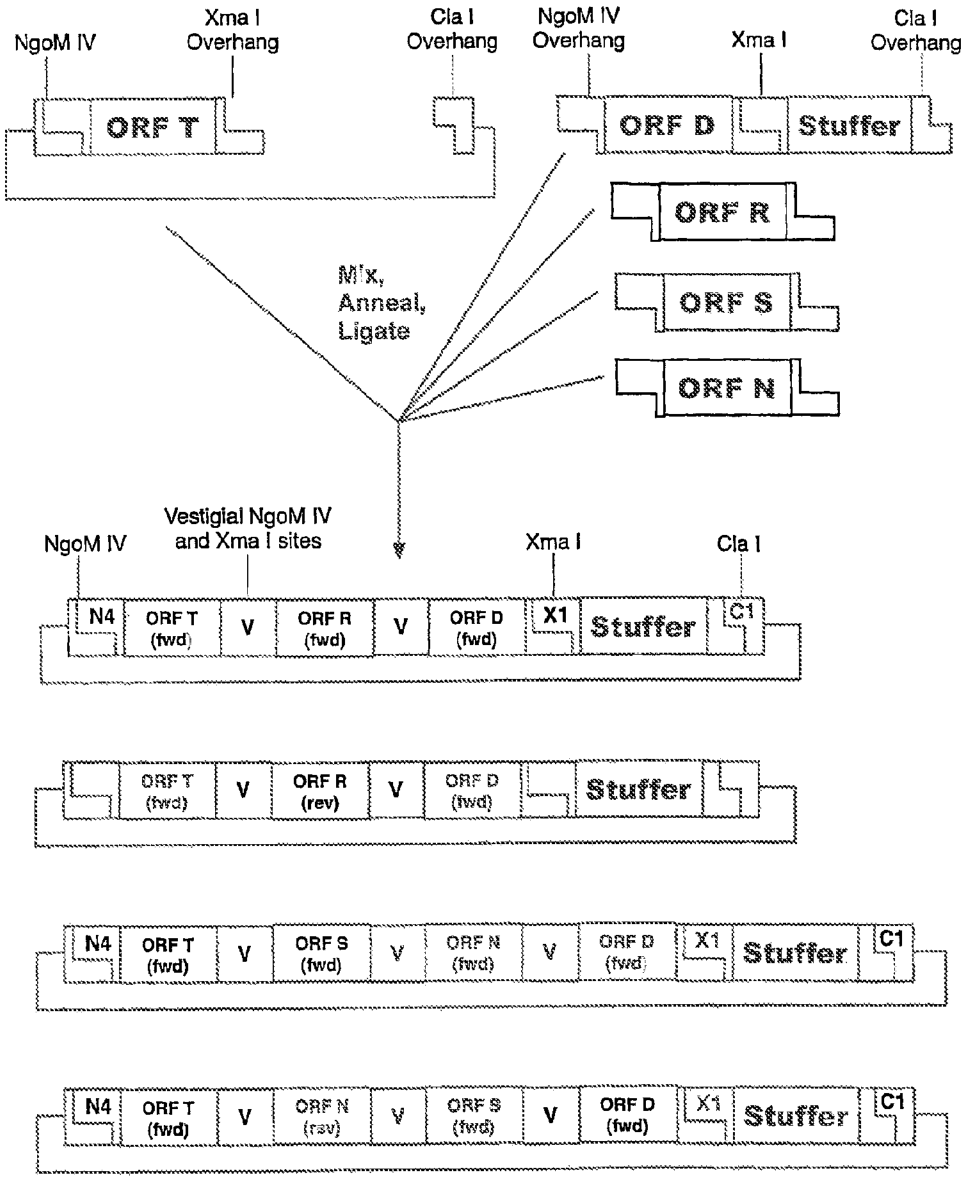
FIG. 13 shows a method of making fusion proteins by dynamic combinatorial synthesis. Abbreviations in this figure are as follows: N4 stands for NgoM IV; X1 stands for Xma I; C1 stands for Cla I; fwd means forward; rev means reverse; V stands for vestigial NgoM IV and Xma I sites.

FIG. 13 is a non-limiting illustration of dynamic combinatorial synthesis. This figure represents only a few possible fusion protein constructs that may result from the method. One skilled in the art recognizes that numerous additional fusion protein constructs will result.

In one embodiment, the invention encompasses a vector comprising each of the following elements arranged sequentially to form a module open reading frame, said vector comprising a) a first restriction site that codes for a first group of amino acids, wherein the first group of amino acids comprises at least two amino acids;

b) a first open reading frame coding for a polypeptide of interest, wherein the coding sequence of the polypeptide of interest is in frame with the coding sequence of at least two amino acids of the first restriction site;

c) a second restriction site that codes for a second group of amino acids, wherein the second group of amino acids comprises at least two amino acids, wherein the coding sequence of the second group of amino acids of the second restriction site is in frame with the coding sequence of the polypeptide of interest of the first open reading frame, and wherein the polynucleotide sequence of the second restriction site is not the same as the polynucleotide sequence of the first restriction site;

d) a spacer polynucleotide sequence, wherein the spacer polynucleotide sequence codes for at least three spacer amino acids, and wherein the coding sequence for the spacer sequence is in frame with the polynucleotide sequence of the second restriction site; and e) a third restriction site that codes for a third group of amino acids, wherein the third group of amino acids comprises at least two amino acids, wherein the coding sequence of the third group of amino acids of the third restriction site are in frame with the coding sequence of the at least three spacer amino acids and wherein the polynucleotide sequence of the third restriction site is not the same as the polynucleotide sequence of the first restriction site and the third restriction site is not the same as the polynucleotide sequence of the second restriction site, wherein elements (a) through (e) are in-frame linked to one another to form the module open reading frame.

In another embodiment, the invention comprises a vector wherein the elements are arranged in a 5' to 3' direction, wherein element (a) is at the 5' end of the vector. Another embodiment encompasses a vector of claim wherein the elements are arranged in a 3' to 5' direction, wherein element (a) is at the 3' end of the vector.

In another embodiment, the invention encompasses a vector further comprising a promoter operably linked to the 5' portion of said module open reading frame. The promoter may be a bacterial or mammalian promoter. Other embodiments encompass a vector further comprising an untranslated region that is 3' to the third restriction site.

In another embodiment, the invention encompasses a vector wherein there are no restriction sites in any of the open reading frames between the first and second restriction groups that occur in either the first or second restriction sites.

In another embodiment, the invention encompasses a method of making a fusion polypeptide comprising, a) digesting the vector from above with restriction enzymes that recognize the second and third restriction sites to create a linear vector with a first and second single-stranded overhang, wherein the first and second overhangs are incompatible with one another;

b) providing a first insert, wherein the first insert comprise at least one additional open reading frame, wherein the at least one additional open reading frame comprises 5' and 3' overhangs that are compatible with the first and second overhangs, wherein each of the at least one additional open reading frames codes for at least one additional polypeptide of interest;

c) ligating the first insert into the linear vector to form a ligated expression vector, wherein the ligation of the 5' overhang of the at least one open reading frame anneals with the first single-stranded overhang of the linear vector, wherein the ligation of the 3' overhang of the at least one open reading frame anneals with the second single-stranded overhang of the linear vector, and wherein the ligation of the 3' overhang recreates the third restriction site, wherein the first open reading frame at the at least one additional open reading frames are ligated in frame with one another.

In another embodiment, the invention encompasses a method of making a fusion polypeptide comprising, a) digesting the ligated expression vector from above, with restriction enzymes that recognize the additional and the recreated third restriction sites to create a linear vector with a third and fourth single-stranded overhang, wherein the third and fourth overhangs are incompatible with one another;

b) providing a second insert, wherein the second insert comprise at least one additional open reading frame, wherein the at least one additional open reading frame comprises 5' and 3' overhangs that are compatible with the third and fourth overhangs, wherein each of the at least one additional open reading frames codes for at least one additional polypeptide of interest;

c) ligating the second insert into the linear vector to form a new ligated expression vector, wherein the ligation of the 5' overhang of the at least one open reading frame anneals with the third single-stranded overhang of the linear vector, wherein the ligation of the 3' overhang of the at least one open reading frame anneals with the fourth single-stranded overhang of the linear vector, and wherein the ligation of the 3' overhang recreates the third restriction site, wherein the all open reading frames are in frame with one another.

In another embodiment, the invention encompasses a method of making a fusion polypeptide comprising a) digesting the vector of above with restriction enzymes that recognize the second and third restriction sites to create a linear vector with a first and second single-stranded overhang, wherein the first and second overhangs are incompatible with one another;

b) providing a first insert, wherein the first insert comprise at least one additional open reading frame, wherein the at least one additional open reading frame comprises 5' and 3' overhangs that are compatible with the first and second overhangs, wherein each of the at least one additional open reading frames codes for at least one additional polypeptide of interest;

c) ligating the first insert into the linear vector to form a ligated expression vector, wherein the ligation of the 5' overhang of the at least one open reading frame anneals with the first single-stranded overhang of the linear vector, wherein the ligation of the 3' overhang of the at least one open reading frame anneals with the second single-stranded overhang of the linear vector, and wherein the ligation of the 3' overhang recreates the third restriction site, wherein the first open reading frame at the at least one additional open reading frames are ligated in frame with one another.

Further embodiments of the invention encompass a method of making fusion protein DNA constructs comprising, a) providing first and second polynucleotide reagents, wherein each reagent contains an open reading frame of interest, and wherein each open reading frame of interest is flanked by at least 3 predetermined restriction endonuclease sites, and wherein 2 of the predetermined sites have compatible overhangs, b) digesting the first polynucleotide reagent with 2 different restriction endonucleases that cleave at 2 of the predetermined restriction endonuclease sites, generating a polynucleotide with 2 different overhangs, c) digesting the second polynucleotide reagent with 2 different restriction endonucleases that cleave at 2 of the predetermined restriction endonuclease sites, wherein a polynucleotide containing an open reading frame of interest is released, wherein the released polynucleotide has 2 different overhangs, and wherein one of the overhangs is compatible with an overhang of the polynucleotide digested in step b), d) mixing together, annealing, and ligating the polynucleotide generated in step b) and the released polynucleotide containing an open reading frame of interest of step c), wherein a third polynucleotide containing a fusion of open reading frames is generated, wherein a junction between the open reading frames of interest is no longer susceptible to digestion with any of the endonucleases that cut at the 3 predetermined restriction sites, and wherein sequences flanking the fusion of open reading frames of interest contain the 3 predetermined restriction sites.

In this method, first polynucleotide may be circular DNA. Furthermore, in this method, the first and second polynucleotides are circular DNA. Additionally, the predetermined restriction sites may be recognition sequences for NgoM IV, Xma I, and Cla I.

The method may be repeated recursively, by repeating steps a) through d), wherein the first polynucleotide provided in step a) is replaced by the third polynucleotide generated in step d).

Additional embodiments encompass a method of making fusion protein DNA constructs comprising, a) providing first and second polynucleotide reagents, wherein each reagent contains an open reading frame of interest, and wherein each open reading frame of interest is flanked by at least 3 predetermined restriction endonuclease sites, and wherein 2 of the predetermined sites have compatible overhangs, b) digesting the first polynucleotide reagent with 2 different restriction endonucleases that cleave at 2 of the predetermined restriction endonuclease sites, generating a polynucleotide with 2 incompatible overhangs, c) digesting the second polynucleotide reagent with 2 different restriction endonucleases that cleave at 2 of the predetermined restriction endonuclease sites, wherein 1 of the restriction endonucleases is identical to a restriction endonuclease of step b), and wherein a polynucleotide containing an open reading frame of interest is released, and wherein the released polynucleotide has 2 incompatible overhangs, d) mixing together, annealing, and ligating the polynucleotide generated in step b) and the released polynucleotide containing an open reading frame of interest of step c), wherein a third polynucleotide containing a fusion of open reading frames is generated, wherein the fusion of open reading frames of interest is flanked by said predetermined restriction sites, and wherein a junction between the open reading frames of interest lacks said 3 predetermined restriction endonuclease sites.

Another aspect of the invention is a library of isolated polynucleotides, wherein each polynucleotide contains an open reading frame of interest flanked by at least 3 predetermined restriction endonuclease sites, and wherein 2 of the 3 predetermined restriction sites are incompatible with each other, and wherein 2 of the 3 predetermined restriction sites are compatible with each other, and wherein each open reading frame of interest lacks the predetermined restriction sites. More specifically, the library contains polynucleotides, wherein each polynucleotide contains an open reading frame of interest, and wherein each open reading frame of interest is flanked on one end by a sequence cleavable by NgoM IV, and wherein each open reading frame of interest is flanked on the other end by sequences cleavable by Xma I and Cla I, and wherein the open reading frame of interest lacks sequences cleavable by NgoM IV, Xma I and Cla I.

The invention also encompasses vectors comprising these isolated polynucleotide, and host cells comprising said vectors.

Figure 14A:
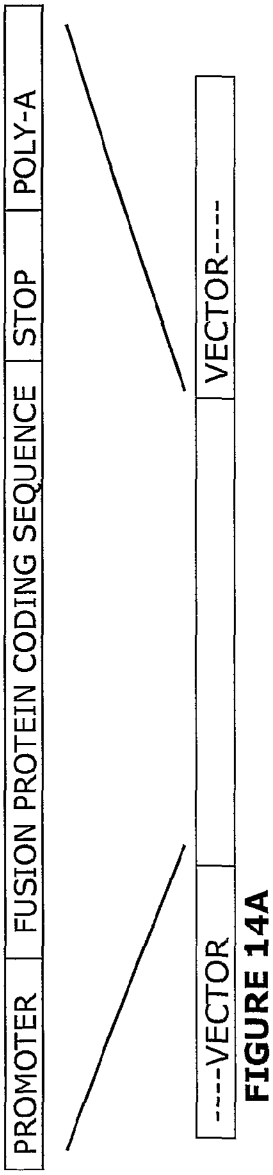
FIGS. 14A-14D show examples of vectors containing modular, chimeric polypeptide gene constructs.

FIG. 14A shows a vector containing a chimeric protein gene construct, wherein the gene construct is releasable from the vector as a unit useful for generating transgenic animals. For example, the gene construct, or transgene, is released from the vector backbone by restriction endonuclease digestion. The released transgene is then injected into pronuclei of fertilized mouse eggs; or the transgene is used to transform embryonic stem cells. The vector containing a gene construct of FIG. 14A is also useful for transient transfection of the trangene, wherein the promoter and codons of the transgene are optimized for the host organism.

Figure 14B:
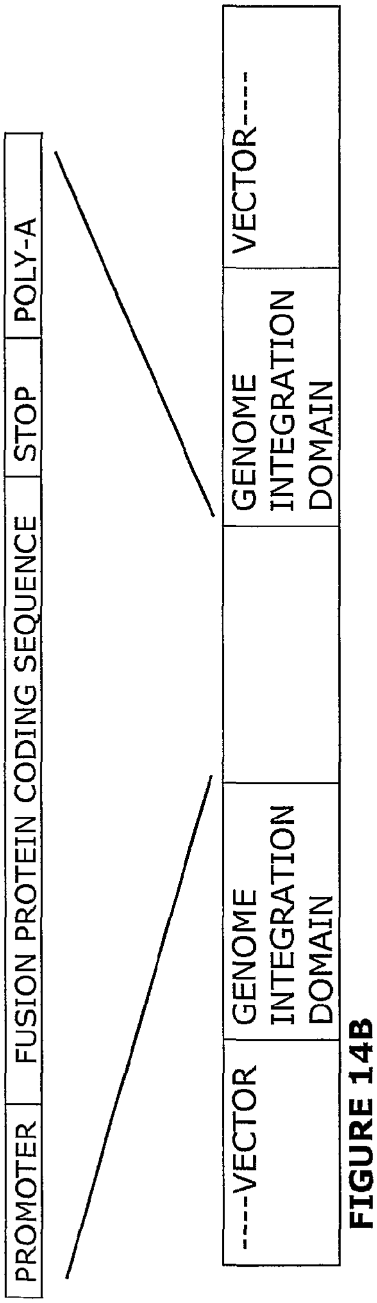
Figure 14C:
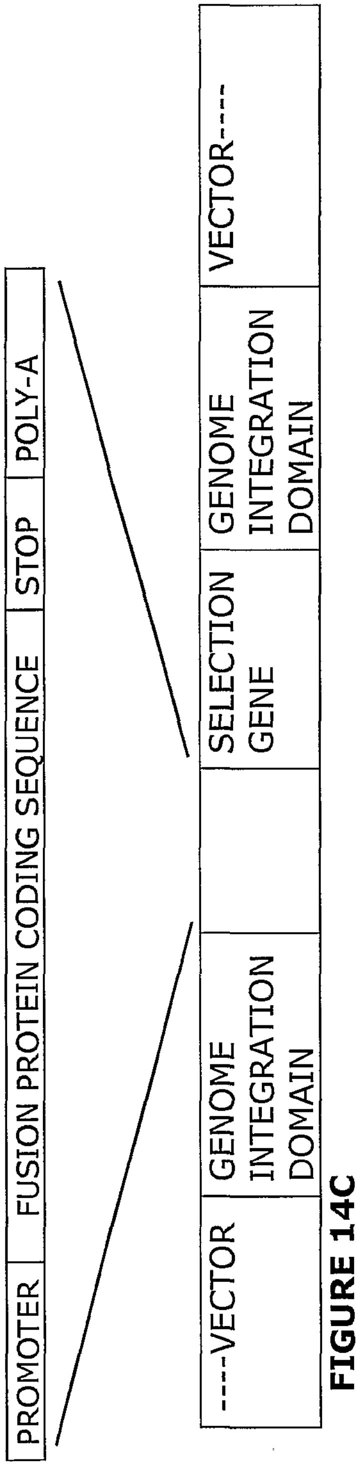

Polynucleotide sequences linked to the gene construct in FIGS. 14B and 14C include genome integration domains to facilitate integration of the transgene into a viral genome and/or host genome.

Figure 14D:
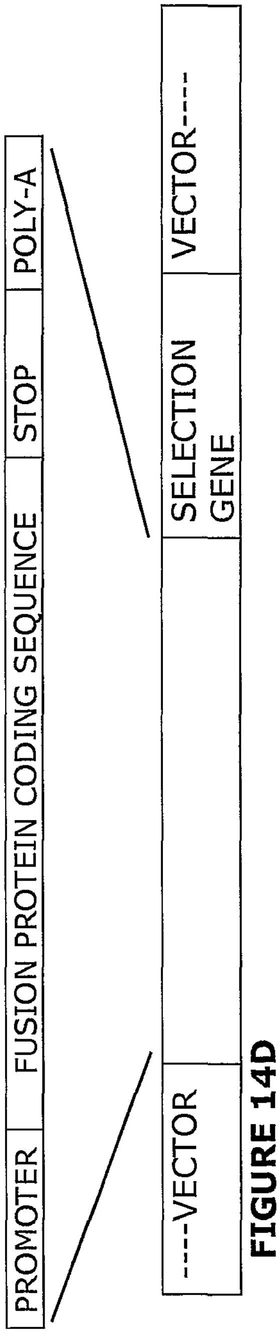

FIG. 14D shows a vector containing a chimeric protein gene construct useful for generating stable cell lines.

What is claimed is:

1. A vector comprising each of the following elements arranged sequentially to form a module open reading frame, said vector comprising a) a first restriction site that codes for a first group of amino acids, wherein the first group of amino acids comprises at least two amino acids;

b) a first open reading frame coding for a polypeptide of interest, wherein the coding sequence of the polypeptide of interest is in frame with the coding sequence of at least two amino acids of the first restriction site;

c) a second restriction site that codes for a second group of amino acids, wherein the second group of amino acids comprises at least two amino acids, wherein the coding sequence of the second group of amino acids of the second restriction site is in frame with the coding sequence of the polypeptide of interest of the first open reading frame, and wherein the polynucleotide sequence of the second restriction site is not the same as the polynucleotide sequence of the first restriction site;

d) a spacer polynucleotide sequence, wherein the spacer polynucleotide sequence codes for at least three spacer amino acids, and wherein the coding sequence for the spacer sequence is in frame with the polynucleotide sequence of the second restriction site; and e) a third restriction site that codes for a third group of amino acids, wherein the third group of amino acids comprises at least two amino acids, wherein the coding sequence of the third group of amino acids of the third restriction site are in frame with the coding sequence of the at least three spacer amino acids and wherein the polynucleotide sequence of the third restriction site is not the same as the polynucleotide sequence of the first restriction site and the third restriction site is not the same as the polynucleotide sequence of the second restriction site, wherein elements (a) through (e) are in-frame linked to one another to form the module open reading frame, wherein the first restriction site is susceptible to a restriction enzyme that would produce a first single-stranded overhang comprising at least 2 nucleotides, wherein the second restriction site is susceptible to a restriction enzyme that would produce a second single-stranded overhang comprising at least 2 nucleotides, wherein said first and second overhangs are complementary to one another, whereupon the annealing of the first and second overhangs, the first restriction site and the second restriction site are destroyed, and wherein the third restriction site is susceptible to a restriction enzyme that would not produce an overhang compatible with the overhang resulting from the restriction of the first restriction site or the overhang resulting from the restriction of second restriction site.

2. The vector of claim 1, wherein the elements are arranged in a 5' to 3' direction, wherein element (a) is at the 5' end of the vector.

3. The vector of claim 1, wherein the elements are arranged in a 3' to 5' direction, wherein element (a) is at the 3' end of the vector.

4. The vector of claim 1, wherein the polypeptide of interest is selected from the group consisting of a full length protein or polypeptide, a protein functional domain, a protein structural domain, a protein enzymatic domain, a protein inhibition domain, a protein binding domain, a protein localization domain, and an epitope.

5. The vector of claim 4, wherein said polypeptide of interest is a protein localization domain.

6. The vector of claim 1, wherein said first restriction site comprises a polynucleotide sequence recognized by an NgoM IV restriction enzyme.

7. The vector of claim 6, wherein the second restriction site comprises a polynucleotide sequence recognized an Xma I restriction enzyme.

8. The vector of claim 7, wherein the third restriction site comprises a polynucleotide sequence recognized by a Cla I restriction enzyme.

9. The vector of claim 8, wherein the spacer polynucleotide sequence codes for three glycine amino acids.

10. The vector of claim 1 further comprising a promoter operably linked to the 5' portion of said module open reading frame.

11. The vector of claim 10, wherein said promoter is a bacterial promoter.

12. The vector of claim 10, wherein said promoter is a mammalian promoter.

13. The vector of claim 10, further comprising an untranslated region that is 3' to the third restriction site.

14. The vector of claim 1, wherein said first open reading frame is immediately adjacent to said second restriction site.

15. The vector of claim 1, wherein said first open reading frame is not immediately adjacent to said second restriction site.

16. The vector of claim 15, wherein at least one additional open reading frame is inserted between the first open reading frame and the second restriction site, wherein each of the at least one additional open reading frames is in frame with both the first open reading frame and the second restriction site, and wherein each of the additional open reading frames codes for at least one additional polypeptide of interest.

17. The vector of claim 16, wherein there are no restriction sites in any of the open reading frames between the first and second restriction sites.

18. The vector of claim 17, wherein the vector comprises at least two additional open reading frames.

19. The vector of claim 18, wherein the vector comprises at least three additional open reading frames.

20. A method of making a fusion polypeptide comprising a) digesting the vector of claim 1 with restriction enzymes that recognize the second and third restriction sites to create a linear vector with a first and second single-stranded overhang, wherein the first and second overhangs are incompatible with one another;

b) providing a first insert, wherein the first insert comprises at least one additional open reading frame, wherein the at least one additional open reading frame comprises 5' and 3' overhangs that are compatible with the first and second overhangs, wherein each of the at least one additional open reading frames codes for at least one additional polypeptide of interest;

c) ligating the first insert into the linear vector to form a ligated expression vector, wherein the ligation of the 5' overhang of the at least one open reading frame anneals with the first single-stranded overhang of the linear vector, wherein the ligation of the 3' overhang of the at least one open reading frame anneals with the second single-stranded overhang of the linear vector, wherein the ligation of the 3' overhang recreates the third restriction site, and wherein the first open reading frame at and the at least one additional open reading frames are ligated in frame with one another.

21. The method of claim 20, wherein the first insert further comprises at least one additional spacer polynucleotide sequence and comprises an additional restriction site that is recognized by the same restriction site that recognizes the second restriction site.

22. The method of claim 21, further comprising a) digesting the ligated expression vector with restriction enzymes that recognize the additional and the recreated third restriction sites to create a linear vector with a third and fourth single-stranded overhang, wherein the third and fourth overhangs are incompatible with one another;

b) providing a second insert, wherein the second insert comprises at least one additional open reading frame, wherein the at least one additional open reading frame comprises 5' and 3' overhangs that are compatible with the third and fourth overhangs, wherein each of the at least one additional open reading frames codes for at least one additional polypeptide of interest;

c) ligating the second insert into the linear vector to form a new ligated expression vector, wherein the ligation of the 5' overhang of the at least one open reading frame anneals with the third single-stranded overhang of the linear vector, wherein the ligation of the 3' overhang of the at least one open reading frame anneals with the fourth single-stranded overhang of the linear vector, wherein the ligation of the 3' overhang recreates the third restriction site, and wherein all open reading frames are in frame with one another.

23. A method of making a fusion polypeptide comprising a) digesting the vector of claim 8 with restriction enzymes that recognize the second and third restriction sites to create a linear vector with a first and second single-stranded overhang, wherein the first and second overhangs are incompatible with one another;

b) providing a first insert, wherein the first insert comprises at least one additional open reading frame, wherein the at least one additional open reading frame comprises 5' and 3' overhangs that are compatible with the first and second overhangs, wherein each of the at least one additional open reading frames codes for at least one additional polypeptide of interest;

c) ligating the first insert into the linear vector to form a ligated expression vector, wherein the ligation of the 5' overhang of the at least one open reading frame anneals with the first single-stranded overhang of the linear vector, wherein the ligation of the 3' overhang of the at least one open reading frame anneals with the second single-stranded overhang of the linear vector, wherein the ligation of the 3' overhang recreates the third restriction site, and wherein the first open reading frame and the at least one additional open reading frames are ligated in frame with one another.

24. A recombinant host cell comprising the vector of claim 1.

25. The vector of claim 4, wherein the full length protein is selected from the group consisting of a kinase, a kinase subunit, a phosphatase, a phosphatase subunit, a peptide ligand, a protease, a protease subunit, an enzyme subunit, a DNA binding protein subunit, a G-protein subunit, an ion channel subunit, and a membrane receptor subunit.

26. The vector of claim 4, wherein the protein functional domain is selected from the group consisting of a DNA binding domain, a transcription activation domain, a dimerization domain, a catalytic domain, a phosphorylation domain, a regulatory domain, a death domain, a pleckstrin homology domain, a lipid binding domain, a hormone binding domains, a ligand binding domain, a zinc finger region, a leucine zipper region, a g-protein binding domain, a glycosylation domain, an acylation domain, and a transmembrane domain.

27. The vector of claim 4, wherein the protein structural domain is selected from the group consisting of an alpha helical region, a beta sheet region, an acidic region, a basic region, a hydrophobic domain, an intra-chain disulfide bonding domain, a co-factor binding domain, and a metal ion binding domain.

28. The vector of claim 4, wherein the protein enzymatic domain is selected from the group consisting of an enzyme active site, a phosphorylation catalytic domain, a phosphatase catalytic domain, an adenylate cyclase catalytic domain, a metabolic enzyme active site, a protease active site, a polymerase active site, a lipase active site, a glycolytic pathway enzyme active site, a nucleotide synthesis enzyme active sites, and an amino acid synthesis enzyme active site.

29. The vector of claim 4, wherein the protein inhibition domain is selected from the group consisting of a kinase inhibitory subunit binding region, a phosphatase inhibitory subunit binding region, and an allosteric ligand binding region.

30. The vector of claim 4, wherein the protein binding domain is selected from the group consisting of a steroid hormone binding domain, a peptide hormone binding domain, a substrate binding domain, an ATP binding domain, a PDZ domain, a SH3 domain, a SH2 domain, a PB1 domain, a drug binding domain, a G-protein binding domain, a DNA binding domain, a lipid binding domain, a carbohydrate binding domain, and a dimerization domains.

31. The vector of claim 5, wherein the protein localization domain is selected from the group consisting of an endoplasmic reticulum localization signal, a nuclear localization signal, a mitochondrial localization signal, a plasma membrane localization signal, and a sarcoplasmic reticulum localization signal.

32. The vector of claim 4, wherein the epitope is selected from the group consisting of a hemagluttinin epitope, a c-Myc epitope, a FLAG, His6, an acidic region, a basic region, and an antibody binding regions.

33. The vector of claim 1, wherein said spacer polynucleotide sequence is adjacent to said second restriction site, and wherein said third restriction site is adjacent to said spacer polynucleotide sequence.

* * * * *

UNITED STATES PATENT AND TRADEMARK OFFICE

CERTIFICATE OF CORRECTION

PATENT NO. : 8,603,807 B2
APPLICATION NO. : 12/090463
DATED : December 10, 2013
INVENTOR(S) : Thomas D. Reed It is certified that error appears in the above-identified patent and that said Letters Patent is hereby corrected as shown below:

In the Claims

In Column 19

Line 47 please replace "frame at and the" with --frame and the--

Signed and Sealed this
Twenty-seventh Day of May, 2014

Michelle K. Lee
*Deputy Director of the United States Patent and Trademark Office*

UNITED STATES PATENT AND TRADEMARK OFFICE

CERTIFICATE OF CORRECTION

PATENT NO. : 8,603,807 B2
APPLICATION NO. : 12/090463
DATED : December 10, 2013
INVENTOR(S) : Reed It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 644 days.

Signed and Sealed this
Twenty-first Day of April, 2015

Michelle K. Lee
*Director of the United States Patent and Trademark Office*

SEQUENCE LISTING

```
<160> NUMBER OF SEQ ID NOS: 9

<210> SEQ ID NO 1
<211> LENGTH: 45
<212> TYPE: DNA
```

<213> ORGANISM: Artificial Sequence
<220> FEATURE:
<223> OTHER INFORMATION: Synthetic chimeric

<400> SEQUENCE: 1
gccggcaaga agaaaaagaa gaagcccggg ggcggaggca tcgat 45

<210> SEQ ID NO 2
<211> LENGTH: 15
<212> TYPE: PRT
<213> ORGANISM: Artificial Sequence
<220> FEATURE:
<223> OTHER INFORMATION: Synthetic chimeric

<400> SEQUENCE: 2

Ala Gly Lys Lys Lys Lys Lys Lys Pro Gly Gly Gly Gly Ile Asp
1 5 10 15

<210> SEQ ID NO 3
<211> LENGTH: 9
<212> TYPE: DNA
<213> ORGANISM: Artificial Sequence
<220> FEATURE:
<223> OTHER INFORMATION: Synthetic spacer

<400> SEQUENCE: 3 ggaggcgga 9

<210> SEQ ID NO 4
<211> LENGTH: 6
<212> TYPE: DNA
<213> ORGANISM: Artificial Sequence
<220> FEATURE:
<223> OTHER INFORMATION: Synthetic NgoM IV recognition sequence

<400> SEQUENCE: 4 gccggc 6

<210> SEQ ID NO 5
<211> LENGTH: 18
<212> TYPE: DNA
<213> ORGANISM: Artificial Sequence
<220> FEATURE:
<223> OTHER INFORMATION: Synthetic ORF recogition sequence

<400> SEQUENCE: 5
aagaagaaaa agaagaag 18

<210> SEQ ID NO 6
<211> LENGTH: 6
<212> TYPE: PRT
<213> ORGANISM: Artificial Sequence
<220> FEATURE:
<223> OTHER INFORMATION: Synthetic ORF recogition sequence

<400> SEQUENCE: 6

Lys Lys Lys Lys Lys Lys
1 5

<210> SEQ ID NO 7
<211> LENGTH: 6
<212> TYPE: DNA
<213> ORGANISM: Artificial Sequence
<220> FEATURE:
<223> OTHER INFORMATION: Synthetic Xma I recogition sequence

<400> SEQUENCE: 7

-continued

```
cccggg                                                                   6


<210> SEQ ID NO 8
<211> LENGTH: 9
<212> TYPE: DNA
<213> ORGANISM: Artificial Sequence
<220> FEATURE:
<223> OTHER INFORMATION: Synthetic spacer

<400> SEQUENCE: 8

ggcggaggc                                                                9


<210> SEQ ID NO 9
<211> LENGTH: 6
<212> TYPE: DNA
<213> ORGANISM: Artificial Sequence
<220> FEATURE:
<223> OTHER INFORMATION: Synthetic Cla I recogition sequence

<400> SEQUENCE: 9

atcgat                                                                   6
```